United States Patent [19]

Davydov et al.

[11] Patent Number: 4,529,589
[45] Date of Patent: Jul. 16, 1985

[54] PHARMACEUTICAL COMPOSITION FOR THE TREATMENT OF DIABETES MELLITUS

[76] Inventors: Anatoly B. Davydov, ulitsa Krasny Kazanets, 19, korpus 1, kv. 283; Eduard A. Babaian, ulitsa Novatorov, 40, korpus 2, kv. 50, both of Moscow; Vladimir I. Metelitsa, Jubileiny prospekt, 35, kv. 186, Khimki Moskovskoi oblasti; Tamara P. Ostrovskaya, ulitsa 1905 goda, 25, kv. 80, Moscow; Rustam I. Utyamyshev, Prospekt Mira, 118, kv. 222, Moscow; Gennady L. Khromov, 2 Frunzenskaya ulitsa, 10, kv. 100, Moscow; Evgeny I. Chazov, Petroverigsky pereulok, 10, Moscow, all of U.S.S.R.

[21] Appl. No.: 536,578

[22] Filed: Sep. 29, 1983

Related U.S. Application Data

[63] Continuation of Ser. No. 363,586, Mar. 30, 1982, abandoned.

[30] Foreign Application Priority Data

Jul. 14, 1981 [SU]  U.S.S.R. ............... 3303301

[51] Int. Cl.³ ............ A61K 37/26; A61K 31/78; A61K 31/79; A61K 9/20
[52] U.S. Cl. ............ 424/81; 424/14; 424/16; 424/19; 424/22; 424/28; 424/78; 424/80; 424/81; 514/3; 514/866
[58] Field of Search ........... 424/19–27, 424/78–81, 178

[56] References Cited

U.S. PATENT DOCUMENTS

| | | | |
|---|---|---|---|
| 1,547,515 | 7/1925 | Murlin | 424/178 |
| 2,474,729 | 6/1949 | Durel et al. | 424/178 |
| 2,789,080 | 4/1957 | Christenson | 424/178 |
| 3,060,093 | 10/1962 | Poulsen et al. | 424/178 |
| 3,312,594 | 4/1967 | Cyr et al. | 424/178 |
| 3,429,308 | 2/1969 | Russell | 128/1 |
| 3,444,858 | 5/1969 | Russell | 128/260 |
| 3,870,790 | 3/1975 | Lowey et al. | 424/178 |
| 3,978,201 | 8/1976 | Khromov et al. | 424/81 |
| 4,059,686 | 11/1977 | Tanaka et al. | 424/19 |
| 4,250,163 | 2/1981 | Nagai et al. | 424/81 |
| 4,292,299 | 9/1981 | Suzuki et al. | 424/16 |

FOREIGN PATENT DOCUMENTS

| | | |
|---|---|---|
| 1060085 | 2/1967 | United Kingdom . |
| 2021610A | 12/1979 | United Kingdom ............ 424/80 |
| 295559 | 2/1971 | U.S.S.R. . |
| 504766 | 2/1976 | U.S.S.R. . |
| 806037 | 2/1981 | U.S.S.R. . |
| 810241 | 3/1981 | U.S.S.R. ............ 424/28 |

OTHER PUBLICATIONS

Ishida et al, Chemical & Pharmaceutical Bulletin, 29(3): 810–816, Mar. 1981.
New Mucosal Dosage form of Insulin, Biol. Abstr. 72(6) #40465, Sep. 15, 1981.
Nuritdinov Vestnik Oftalmocogi, 5: 59–60 (1980) Polyacrylamide as a Base for Mecicinal Eye Films.
Maichuk Symposium on Ocular Therapy, 9: 1–16 (1976) "Sodisulfapyridazine (pp. 10–15)", Polymeric Drug Delivery Systems in Ophthalmology, John Wiley & Sons, NY, NY.
Societe, C.A. 77, #52346b (1972) Heinze, C.A. 79, #27969i (1973) Fraser, C.A. 84, #99656n (1976) Curry, C.A. 71, #109488g (1969).
Kaplan C.A., 82, #152763g (1975) U3 Katkovskii, CA. 75, #91298j (1971).
Das, C.A., 79, #27063r (1973).
Barlow, C.A., 25, #3397(I) (1931).
Gortinskaya, C.A., 85, #33058h (1976).
Askelof, C.A., 40, #3472(g) (1946).

*Primary Examiner*—Shep K. Rose
*Attorney, Agent, or Firm*—Burgess, Ryan & Wayne

[57] ABSTRACT

A pharmaceutical preparation for the treatment of diabetes mellitus comprising the following components, in percent by weight:

| | |
|---|---|
| crystalline insulin with a conventional activity of 1 mg = 20 units | 1 to 25.0 |
| additives inhibiting deactivation of insulin, viz. 5-(para-[N—(3-methoxypyridazinyl-6)-sulphamido]-phenylazo)-salicylic acid, calcium gluconate or a mixture thereof | 0.02 to 10.0 |
| preservatives | 0.1 to 15.0 |
| additives adjusting solubility of insulin | 0.01 to 10.0 |
| water-soluble polymeric base | the balance. |

12 Claims, No Drawings

PHARMACEUTICAL COMPOSITION FOR THE TREATMENT OF DIABETES MELLITUS

This application is a continuation of application Ser. No. 363,586, filed Mar. 30, 1982 now abandoned.

FIELD OF THE INVENTION

The present invention relates to the art of pharmacy and, more specifically, to a novel pharmaceutical preparation for the treatment of diabetes mellitus.

BACKGROUND OF THE INVENTION

Well known in the art is the use of insulin preparations in medical practice for the treatment of patients suffering from diabetes mellitus.

Currently known are certain derivatives of insulin preparations such as an aqueous solution of crystalline insulin (for injections). Other insulin derivatives are known, such as insulin for injections which differs from the preceding one only by its origin-from whale pancreas in contrast to cattle and pig pancreas as in the first preparation; sousinsulin (actrapid) produced from pig's pancreas; and an insulin preparation consisting of crystalline insulin dissolved in water and acidified with hydrochloric acid and also containing 1.6–1.8% of glycerol and 0.25 to 0.3% of a preservation agent-phenol, the solution pH being equal to 3.0–3.5. All these pharmaceutical preparations are administered hypodermally as injection solutions, intramuscularly or intravenously.

Also known in the art is an insulin preparation having a prolonged action. The preparation—a solution of protaminezinc-insulin for injections comprising a mixture of a solution of crystalline insulin, a solution of protamine, zinc chloride and sodium phosphate, as well as about 1.6% by weight of glycerol and phenol as a preservation agent is used. Likewise, the afore-mentioned preparations are administered by injection.

The suspension preparation that is, insulin-protamine for injections comprises, in addition to insulin, protamine sulphate, and sodium phosphate disubstituted. The preparation comprises a suspension which is treated with preservation agents such as metacresol, phenol and Nipagin (ethyl-p-hydroxybenzoate) with the addition of glycerol. The preparation is administered by injection only.

Also known in the art is the preparation insulindes containing a suspension of insulin with a low-molecule polyvinylpyrrolidone and zinc chloride in a phosphate buffer, as well as a preservation agent-Nipagin with glycerol. The preparation has a prolonged effect and is administered as by hypodermal injections.

The preparation insulincrides comprising a suspension of crystalline insulin with a low-molecular polyvinylpyrrolidone and zinc chloride in an acetate buffer with the addition of a preservation agent; Nipagin also has a prolonged effect and is administered by injections only (cf. M. D. Mashkovsky, "Pharmaceuticals," Moscow, "Medicina" Publishing House, 1977, vol. I, pp. 557–563).

The above-mentioned preparations have a number of disadvantages. They comprise solutions or suspensions of insulin intended for every-day injections which a patient should perform by himself obeying the rules of aseptics and antiseptics using special accessories (syringe, needles). Injections of such preparations are rather painful and frequently are accompanied by complications such as hemorrhages and suppurations due to septic conditions.

Insulin preparations after subcutaneous (or sometimes intramuscular injections) relatively rapidly affect the sugar content in blood; e.g. usual crystalline insulin in the majority of patients causes this effect within 40 to 60 minutes and reaches its maximum effect within 2–5 hours.

After a certain period after eating, in the night time, hypoglycemic states can be developed in patients and in some grave cases even a hypoglycemic coma can occur. A patient suffering from diabetes mellitus must therefore coordinate meal time with administration of the insulin preparations. Irrespective of specific features of the administered preparation, in patients suffering from diabetes mellitus, the character of the sugar curve after meals frequently differs from the normal one.

Apart from injection preparations of insulin, also known are insulin preparations which are administered per os or rectally. Known are insulin preparations to be administered into the intestine which comprise insulin, surfactants in a mixture with phosphates or bile acids, for example, a preparation comprising crystalline insulin, 0.5% of zinc, 3% of surfactant, corn oil, and 0.1% of glycerol. As a surfactant, the preparation comprises 1% of bile acids. The preparation is administered in the form of a suppository which is inserted into the rectum (Ishikawa K., Okata J., Mitomi M. et al. J. Pharm.Pharmacol., 1980, No.32, No.5, p.314–318).

These preparations have a disadvantage residing in an irritating effect on mucous membranes of the gastric-intestine tract, variale bioassimilability depending on numerous biodegradation conditions and absorption in the gastric-intestinal tract, as well as on the degree of metabolism of insulin in liver.

Another disadvantage resides in a the inconvenience of rectal administration and traumatism for the rectum mucous membrane due to repeated daily administration of suppositories. The preparations involving rectal administration have consequently not found a wide application in the treatment of patients suffering from diabetes mellitus.

also known in the art is a preparation of insulin for peroral administration which comprises insulin in combination with synthetic polymers. The polymeric base comprises synthetic water-soluble polymers-polyethylene polyelectrolyte and its copolymers, weak polyelectrolytes of anionic and cationic types and polyvinylpyrrolidone with a molecular weight of from 20,000 to 30,000. The ratio of crystalline insulin to synthetic polymers is equal to 1:1 or 1:5. The preparation also incorporates preservation additives and, as an additive for adjusting insulin solubility, low-molecular surfactants such as sodium laurylsulphate and sodium dodecylsulphate (5% by weight of insulin)/cf. V. G. Baranov, L. L. Schukovskaya, V. A. Kropachev et al. "Endocrinology Problems", Moscow, "Medicina" Publishing House, 1979, vol.25, No.6, p.41–47).

This prior art preparation also has a disadvantage residing in the variable character of its assimilability, depending on numerous variable conditions of biodegradation and absorption in the gastro-intestinal tract, as well as on the degree of metabolism during the first passage through the liver. Furthermore, the preparation does not provide for a sufficient protection of insulin from the effect of enzymes present in saliva. This preparation has not found a wide application in medicinal practice for the treatment of patients suffering from diabetes mellitus.

SUMMARY OF THE INVENTION

It is an object of the present invention to provide a novel pharmaceutical preparation for correction of insulin insufficiency which also adjusts to individual particularities of disturbance of the carbohydrate exchange involving non-injection administration through the mucous membrane of the mouth cavity.

This object is accomplished by pharmaceutical preparation for the treatment of diabetes mellitus comprising insulin, conservation or preservation agents, additives adjusting the solubility of insulin and a water-soluble polymeric base, in accordance with the present invention. There is also present 5-(para-[N-(3-methoxypyridazinyl-6)-sulphamido]-phenylazo)-salicylic acid of the formula:

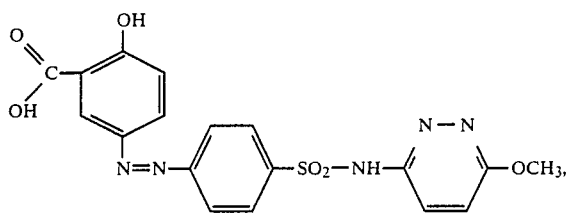

and/or calcium gluconate in the following proportions of the components, in percent by weight:

| | |
|---|---|
| 5-(para-[N—(3-methoxypyridazinyl-6)-sulphamido]-phenylazo)salicylic acid and/or calcium gluconate | 0.02 to 10.0 |
| crystalline insulin with conventional activity of 1 mg = 20 units | 1-25.0 |
| preservatives | 0.1 to 15.0 |
| additives for adjusting insulin solubility | 0.01 to 10.0 |
| water-soluble polymeric base | the balance. |

The pharmaceutical preparation according to the present invention contains the components of 5-(para-[N-(3-methoxypyridazinyl-6)-sulphamido]-phenylazo)-salicyclic acid (salazopyridazine) and calcium gluconate either in combination or separately. These components inhibit deactivation of insulin in the saliva fluid. As the preservatives the pharmaceutical composition according to the present invention, can incorporate phenol or derivatives thereof, albumin or other water-soluble proteins recovered from blood plasma. It preferably incorporates phenol in an amount of from 0.1 to 1%, or albumin in an amount of from 1 to 15%, or a mixture of phenol with albumin in an amount of from 0.1 to 15%. As the additives adjusting insulin solubility, the preparation according to the present invention can incorporate mineral and organic acids including aminoacids as well. It should preferably contain 0.5N hydrochloric acid or acetic acid in an amount ensuring a pH of the mixture within the range of from 2.0 to 4.0 or glycine in an amount of from 1 to 10%. As the water-soluble polymeric base, the preparation according to the present invention contains preferably a copolymer of N-vinylpyrrolidone, acrylamide and ethylacrylate, the components being employed in the following proportions, in percent by weight:

N-vinylpyrrolidone with acrylamide: 70 to 99
ethylacrylate: 1 to 30.

To control the speed of dissolution of the polymeric base, the pharmaceutical preparation according to the present invention, additionally contains glucose or a polyester based on polyethylene glycol and a dibasic acid with a molecular weight of from 2,000 to 5,000 or polyvinylpyrrolidone in an amount of from 2 to 20% by weight of the copolymer.

The pharmaceutical preparation according to the present invention is administered through the mucous membrane of the mouth cavity. The preferred pharmaceutical form of the preparation according to the present invention is plates with a thickness of from 0.1 to 1.5 mm with a content of insulin of from 20 to 150 units. The plate thickness in the abovementioned range is selected as a matter of convenience. The selection of a plate with the required dosage of the active principle is individually made for every patient.

DETAILED DESCRIPTION OF THE INVENTION

The pharmaceutical preparation for the treatment of diabetes mellitus has been studied on volunteer patients-physicians.

The experiments have been performed on 8 volunteers. 58 tests were carried out including 9 control tests without administration of insulin, 6 control tests with subcutaneous administration of insulin and 43 experimental tests with the administration of plates of the preparation according to the present invention.

The control investigation—a sugar curve—has been taken for every volunteer. This involved determination of the blood sugar level in an empty stomach, whereafter the patient was administered glucose per os at the rate of 0.7 g/kg of the body weight diluted with 200 ml of warm water and then the blood sugar level was determined after 30, 60 and 120 minutes. Therefore, in this manner, the blood sugar level variations were determined under the effect of administration of gluclose including the determination of the maximum increase as a percentage of the starting sugar level in blood in the empty-stomach state. After 1–2 weeks, the investigation with a similar sugar load was repeated simultaneously with subcutaneous administration of crystalline insulin at the rate of 0.1–0.2 unit/kg of the body weight right after the administration of the same dose of glucose. After an additional 1–2 weeks, the investigation with the preparation according to the present invention has been carried out.

The preparation according to the present invention in the form of plates of a polymer was placed under the tongue by application of the plates to the lower lingual surface at its root or at any other suitable place of the mucous membrane of the mouth cavity.

The content of insulin in the plates was varied from 8 to 150 units. After a complete resorption of the plate, maximum within 60 minutes, the volunteer was given a standard dose of glucose per os. The blood examination for sugar has been performed on an empty stomach after 30, 60 and 120 minutes since the glucose administration. The hypoglycemic effect of the test preparations was evaluated by the difference in sugar levels in blood (%) as compared to the control test (without insulin).

Patient O. was a healthy woman (60 kg body weight). 10 experiments were performed including 2 control and 8 tests with the preparation according to the present invention. The doses of insulin in plates ranged from 8 to 32 units. The duration of resorption of the plates was 4 to 34 minutes. In the tests with the preparation of this invention, glucose was administered within 1 to 38 minutes.

The hypoglycemic effect in all eight experiments on the average was maximum pronounced after 30 minutes (32.5%); after 60 minutes it was 16.9% and after 120 minutes—24.9%. In all 8 tests a hypoglycemic effect was attained.

Volunteer I. was a healthy woman (73 kg body weight). 11 tests were performed including 2 control tests and 9 experiments with the preparation according to the present invention. The dose of insulin in plates was varied from 8 to 75 units. The duration of resorption of the plates was within the time limit of from 5 to 35 minutes. In tests with the prepration according to the present invention, glucose was administered after 3-40 minutes after complete resorption of the plates. In one experiment the dose of 8 units was insufficient to provide a hypoglycemic effect. After increasing dose in all the remaining 8 tests, this effect was attained. It was most clearly pronounced after 30 minutes—44.2%; after 60 minutes it was 10.1% and after 120 minutes—17.6%.

The insulin test against the background of the sugar load comprising subcutaneous injection of 16 units of crystalline insulin simultaneously with administration of 56 g of glucose has shown that after 30 minutes, the sugar level in blood was increased by 31% relative to the initial value; after 60 minutes—by 13% and after 120 minutes it was reduced by 7%. As compared to the control sugar curve, it has been noted that the injection of 16 units of insulin caused a decrease in the blood sugar level after 30 minutes by 55%, after 60 minutes—by 18% and after 120 minutes—by 34%. In all the tests, there was attained a sufficiently pronounced and uniform hypoglycemic effect.

Volunteer X. was a healthy man (76 kg body weight). 5 tests were performed including 2 control tests and 3 experimental tests, using plates of the preparation according to the present invention. The dose of insulin in the plates was 64 units. The plates were resorbed within 7-20 minutes. Glucose was administered after 9-31 minutes following the resorption of the plates. The hypoglycemic effect was most clearly pronounced after 60 minutes and was 26.3% on the average; after 30 minutes it was equal to 21% and after 120 minutes-12.4%. In all three experiments, a sufficient hypoglycemic effect was attained.

Volunteer H. was a healthy man (70 kg body weight). 3 tests were performed including 1 control test and 2 tests with the preparation according to the present invention. The dose of insulin in the plates was 8 and 64 units. The plates were resorbed within 15 and 27 minutes. Glucose was administered 5 and 21 minutes after resorption of the plates. The hypoglycemic effect obtained in one test with a plate of the preparation of this invention containing 8 units of insulin was evaluated as insufficient. Apparently, the dose of insulin was inadequate for this patient. Upon increase of the dose to 64 units in the second test, a pronounced effect was observed. The sugar curve taken in the second test demonstrated the fact that the sugar level in blood 30 minutes after the administration of glucose was increased by 43% as compared to the initial value; after 60 minutes, it returned to the initial level and after 120 minutes, it was lower than the initial value by 7%. In comparison with the control sugar curve, the blood sugar level after 30 minutes was by 26% lower than in the control; after 60 minutes,—lower by 32% and after 120 minutes it was slightly higher than the initial level (by 11%).

Volunteer D. was a healthy man (74 kg body weight). 8 tests were performed, including 2 control tests and 6—with the preparation of the present invention. The dose of insulin in plates was 8 and 32 units. The time of resorption of the plates was from 16 to 45 minutes. Glucose was administered 1-31 minutes after resorption of the plates. In one test, a dose of 8 units of insulin was insufficient to give the expected effect; upon increase of the dose to 32 units in other 5 tests, a sufficient hypoglycemic effect was obtained. It was most clearly pronounced after 60 minutes by 75.3% on the average; after 30 minutes it was equal to 34.7% and after 120 minutes, the blood sugar level was, on the average, almost the same as the initial level.

Insulin tests against the background of the sugar load with subcutaneous injection of 8 units of crystalline insulin simultaneously with peroral administration of 56 g of glucose has shown that after 30 minutes, the blood sugar level is increased by 86% as compared to the initial value; after 60 minutes—by 40% and after 120 minutes—by 33%. As compared to the control sugar curve, it has been found that the injection of 8 units of insulin has not caused, after 30 minutes, a decrease of the sugar level; at this time, it was even by 6% higher than the control value; after 60 minutes, the sugar level was by 60% below the control level and after 120 minutes, it was by 20% above it.

The sugar level of patient D., in the case of administration of a plate of the preparation of this invention with the content of insulin of 32 units, has shown that the blood sugar level after 30 minutes, was increased only by 7% as compared to the initial sugar level; after 60 minutes and 120 minutes—by 37 and 5%, respectively, as compared to the initial level. Upon comparison of this curve with the control curve, it could be observed that after 30 minutes, the sugar level was below that of the control by 73%; after 60 and 120 minutes—by 63 and 8%, respectively.

Therefore, the preparation according to the present invention ensured a pronounced smooth hypoglycemic effect during two hours of investigation in all points exceeding the corresponding effect of an insulin injection.

Volunteer P. was a healthy woman (body weight 71 kg). 7 tests were performed including 2 control tests and 5 tests with the preparation according to this invention. The doses of insulin in the plates were 16 and 32 units. The time of resorption of the plates was 12 to 45 minutes. Administration of glucose was effected 1-34 minutes thereafter. In the first test, at a content of insulin in the plate of 16 units, the resulting effect was insufficient; when the dose was increased to 32 units in 4 other tests, a sufficient hypoglycemic effect was obtained. It was the highest after 30 minutes—38.5% averaged from 4 tests; after 60 minutes—37.3% and after 120 minutes—3.5%.

The insulin test against the background of the sugar load comprising subcutaneous injection of 8 units of crystalline insulin simultaneously with per os administration of 56 g of glucose has shown that after 30 minutes, the blood sugar level was increased by 87% as compared to the initial value; then after 60 minutes, it was lowered by 53% and after 120 minutes, it returned to the initial level. In comparison of this test with the control investigation, it was noted that the blood sugar level after 30 minutes exceeded the control value by 16%; after 60 minutes it was sharply reduced and was below the control value by 43% and after 120 minutes, it was below the control by 12%.

The sugar curve of patient P., upon administration of a plate of the preparation of this invention with the content of insulin of 32 units, has shown that the blood sugar level after 30 minutes following the loading with glucose, exceeded the initial value by 30%; after 60 minutes—by 25% and after 120 minutes, it was below that the initial value by 17% and was equal to 80 mg %. As regards the absolute value, the blood sugar level varied from 96 mg% (prior to loading with glucose and administration of the plate); to 125 mg% after 30 minutes (maximum) and after 2 hours, it was lowered to 80 mg%. Consequently, within the above-specified time limits, the plate with 32 units of insulin caused the required hypoglycemic effect which was more pronounced than after administration of 8 units of insulin subcutaneously. At the end of the test, after 2 hours, no excessive hypoglycemia was observed (the blood sugar level only insignificantly differed from the initial).

Volunteer Pv. (body weight 89 kg) suffered from diabetes in a light form for 10 years. The blood sugar level in the morning on empty stomach was varied from 125 to 190 mg%. On recommendation of the endocrinologist, he was treated with maninyl in a dose of from 0.00125 to 0.0025 g (¼-½ of a tablet) a day. 6 tests were performed including 1 control sugar curve at the background of administration of a dietic breakfast, the 2-nd test—the same curve but with administration, during breakfast, of 0.00125 g of maninyl and 4 tests with the preparation according to the present invention. The doses of insulin in the plates of the preparation of this invention were 16 to 64 mg. The duration of resorption of the plates was 9 to 36 minutes. The breakfast was 9-37 minutes thereafter. In one test, a noticeable hypoglycemic effect was not attained. In all of the other three experiments, it was observed.

The sugar curve obtained after the control test against the background of having a dietic breakfast without hypoglycemic remedies had the following character: the starting blood sugar level was 125 mg%; after 30 minutes since the breakfast—153 mg%; 60 minutes thereafter—155 mg%, 2 hours thereafter—135 mg%, i.e., after 30 and 60 minutes, the blood sugar level was increased by 22 and 24% respectively relative to the initial value.

In a week, the test was repeated; however, during the dietic breakfast, the volunteer was administered 0.00125 g of maninyl (¼ of a tablet). The sugar curve had a similar character; however, the starting sugar level in blood was higher—155 mg%, and the raise of the curve after 30 and 60 minutes was similar (+29% of the initial value). The absolute level of blood sugar was as high as 200 mg%. After 120 minutes, a high blood sugar level was retained—170 mg% which was by 10% higher than the initial value on the same day of investigation.

One week afterwards, the experiment was repeated. The initial level of blood sugar was equal to 190 mg%. The volunteer was administered a plate of the preparation of this invention containing 16 units of insulin (test dose) sublingually; 30 minutes thereafter, the volunteer had breakfast (dietic one). 30 minutes after the breakfast, the blood sugar level was increased up to 200 mg% (by 5% altogether) which was by 17% below the raise in the control test; after 60 minutes—by 26% (240 mg%) which substantially corresponded to the level raise in the control investigation (+2%) and after 120 minutes—reduced by 8% of the initial value (175 mg%) which was by 16% below the level in the control test. Therefore, in the volunteer with diabetes mellitus for whom the raise in blood sugar level by 21-24% of the starting level after the dietic breakfast is characteristic, the administration of the dose of maninyl prescribed by the endocrinologist provided no hypoglycemic effect at all. The test dose of a plate of the preparation according to the present invention with 16 units of insulin sublingually administered resulted in a moderate hypoglycemic effect.

Volunteer M. was a healthy man (100 kg body weight). 8 tests were carried out including 2 control tests and 6—with the preparation according to the present invention. The doses of insulin in plates of the preparation were 8 to 150 units. The time of resorption of the plates is 9 to 30 minutes. Administration of glucose took place 2-60 minutes after the resorption of the plates. In three tests, the use of plates of the preparation according to the present invention resulted in a hypoglycemic effect (the content of insulin was 64 units). The effect was the highest after 30 minutes—27.3% in three tests on the average; after 60 minutes—8.8%, after 120 minutes—1.3%.

Therefore, out of 43 tests using the preparation according to the present invention, in 35 tests, a sufficient hypoglycemic effect is obtained. In 5 tests on 5 volunteers, the dose of insulin in plates was insufficient to result in a hypoglycemic effect. The use of plates with a high dose of insulin in the subsequent tests, a clearly pronounced hypoglycemic effect was observed.

In 3 tests on volunteer M., the preparation provided no noticeable hypoglycemic effect which is apparently due to the individual response of this patient to the preparation and is one of the possible variants of the norm.

Plates of the preparation of this invention have not caused a heavy hypoglycemic state in any of the test cases. They produced a smooth hypoglycemic effect.

The sublingual administration of the plates has resulted in their immediate glueing to the mucous membrane owing to their adhesive properties. The time of resorption of the plates of the preparation according to the present invention was 4-5 minutes. The plates caused no local undesirable reactions and were neutral as to their organoleptic properties. The hypoglycemic effect of the preparation of this invention was comparable in its manifestation with the effect of insulin in subcutaneous injection, and in some cases, it was even superior to the effect of insulin injections. At the same time, the administration of the preparation according to the present invention has resulted in no heavy hypoglycemic states which are possible in the case of administration of insulin by injections.

The preparation according to the present invention has a number of advantages over the known preparations. The preparation of this invention has a smooth hypoglycemic effect without grave hypoglycemic sequences which makes it possible to treat patients by needle-free methods and to obtain physiological correction of the carbohydrate exchange after each meal consumption, provided that the dosage of the preparation and the time of its administration thereof are established on an individual basis, on condition of the necessity of coincidence of peaks of the sugar curve and pharmacodynamic effect of insulin supplied into the systemic blood circulation. The preparation according to the present invention is especially indispensible for patients suffering from diabetes mellitus in childhood and junior age; it opens opportunities for administration of insulin for the first time in the boundary forms of disturbances of tolerance towards carbohydrates; it enables a strict dosage of insulin ensuring a good assimilation thereof, a mild and lasting effect without sharp reduction of the sugar levels.

The preparation according to the present invention is obtained by successive addition of all the components to the calculated amount of water and mixing of the blend till the formation of a homogeneous solution. In the production of the preparation in the plate form, the solution is applied in one or more layers onto a substrate of an inert material and air dried at a temperature of from 18° to 40° C. to a residual moisture content of not more than 15%. From the dried film, plates are cut-out by means of a punch to a desired shape and size.

For a better understanding of the present invention, some specific examples illustrating embodiments of the pharmaceutical preparation and the method for producing same according to the present invention are given hereinbelow.

EXAMPLE 1

A pharmaceutical composition is prepared which has the following ingredients, in percent by weight:

| | |
|---|---|
| crystalline insulin with the activity of 1 mg = 24.5 units | 0.85 |
| 5-(para-[N—(3-methoxypyridazinyl-6)-sulphamido]-phenylazo)-salicylic acid | 0.02 |
| albumin | 1.0 |
| glycine | 1.0 |
| phenol | 0.1 |
| hydrochloric acid (0.1 N) | 0.01 |
| copolymer of N—vinylpyrrolidone, acrylamide, ethylacrylate with the weight ratio of the two former ingredients to the third of 99:1 | 97.02 |

A 15-20% aqueous solution of the above-specified composition (pH=4.0) prepared by successive addition of all the components to the calculated amount of water and stirring of the mixture till the formation of a homogeneous solution is applied in one or more layers onto a substrate from an inert material and dried in the air at a temperature of 18°-40° C. to a residual moisture content of not more than 15%. From the dried film having thickness of 1.5 mm, oval-shape plates are cut out by means of a punch to the size of 4.5×9 mm. Each plate weights 60 mg and contains 12.5 units of insulin.

EXAMPLE 2

A medicated composition is prepared which has the following ingredients, in percent by weight:

| | |
|---|---|
| crystalline insulin with the activity of 1 mg = 24.2 units | 20 |
| calcium gluconate | 10 |
| phenol | 2 |
| hydrochloric acid (0.5 N) | 0.5 |
| albumin | 10 |
| glycine | 9.5 |
| copolymer of N—vinylpyrrolidone, acrylamide, ethylacrylate having the ratio of the two former components to the third of 70:30 | 48 |

From this composition having a pH of a solution thereof equal to 3.1, oval plates are made in a manner similar to that described in the foregoing Example 1 having a thickness of 0.1 mm. The weight of each plate is 4.2 mg; the content of insulin in each plate is 20 units.

EXAMPLE 3

A pharmaceutical preparation is produced which has the following composition, in percent by weight:

| | |
|---|---|
| crystalline insulin with the activity of 1 mg = 25.2 units | 10 |
| 5-(para-[N—(3-methoxypyridazinyl-6)-sulphamido]-phenylazo)-salicylic acid | 0.05 |
| calcium gluconate | 5.0 |
| phenol | 0.2 |
| acetic acid (0.5 N) | 0.05 |
| albumin | 5.0 |
| glycine | 5.0 |
| copolymer of N—vinylpyrrolidone, acrylamide, ethylacrylate with the weight ratio of the two former components to the third of 80:20 | 59.3 |
| glucose | 15.4 |

From this composition having pH of its solution equal to 3.5, plates are produced in a manner similar to that of Example 1 having a thickness of 0.6 mm and weighing 25 mg each; the content of insulin in each plate is 63 units.

EXAMPLE 4

A pharmaceutical preparation is produced which has the following composition, in percent by weight:

| | |
|---|---|
| crystalline insulin with the activity of 1 mg = 25.2 units | 5.0 |
| 5-(para-[N—(3-methoxypyridazinyl-6)-sulphamido]-phenylazo)-salicylic acid | 0.05 |
| calcium gluconate | 5.0 |
| phenol | 0.2 |
| acetic acid (0.5 N) | 0.05 |
| albumin | 5.0 |
| glycine | 5.0 |
| copolymer similar to that of Example 3 | 63.3 |
| polyester based on polyethylene glycol and succinic acid with a molecular weight of 2,000 | 16.4 |

From this composition having a pH of its solution equal to 3.2, plates are produced as described in Example 1 which have a thickness of 0.6 mm, weight of 25 mg and the content of insulin in each plate is 31.5 units.

EXAMPLE 5

A pharmaceutical preparation is produced which has the following composition, in percent by weight:

| | |
|---|---|
| crystalline insulin with the activity of 1 mg = 25.2 units | 5.0 |
| 5-(para-[N—(3-methoxypyridazinyl-6)-sulpha-mido]-phenylazo-)-salicylic acid | 0.05 |
| calcium gluconate | 5.0 |
| phenol | 0.2 |
| albumin | 14.8 |
| acetic acid (0.5 N) | 0.05 |
| copolymer similar to that of Example 3 | 59.5 |
| polyvinylpyrrolidone | 15.4 |

From this composition having a pH of its solution equal to 2.8, plates are produced as in Example 1 which have each a thickness of 0.6 mm, weight of 25 mg and the content of insulin in each plate is 31.5 units.

EXAMPLE 6

A pharmaceutical preparation is produced which has the following composition, in percent by weight:

| | |
|---|---|
| crystalline insulin with the activity of 1 mg = 25.2 units | 5.0 |
| 5-(para-[N—(3-methoxypyridazinyl-6)-sulphamido]-phenylazo)-salicylic acid | 0.05 |
| calcium gluconate | 5.0 |
| phenol | 0.2 |
| acetic acid (0.5 N) | 0.05 |
| albumin | 5.0 |
| glycine | 5.0 |
| copolymer similar to that of Example 3 | 74.9 |
| glucose | 1.6 |
| polyester based on polyethylene glycol and adipic acid with a molecular weight of 5,000 | 1.6 |
| polyvinylpyrrolidone | 1.6 |

From this composition having a pH of its solution of 3.6, plates are produced as described in Example 1, each having a thickness of 0.6 mm, weight of 25 mg and the content of insulin is 31.5 units.

EXAMPLE 7

A pharmaceutical preparation is produced which has the following composition, in percent by weight:

| | |
|---|---|
| crystalline insulin with the activity of 1 mg = 25.2 units | 6.0 |
| 5-(para-[N—(3-methoxypyridazinyl-6)sulphamido]-phenylazo)-salicylic acid | 0.05 |
| calcium gluconate | 6.0 |
| phenol | 0.1 |
| albumin | 12.0 |
| hydrochloric acid (0.5 N) | 0.05 |
| glycine | 2.4 |
| copolymer similar to that of Example 3 | 50.0 |
| polyvinylpyrrolidone | 9.0 |
| glucose | 2.4 |
| polyester based on polyethylene glycol and succinic acid with the molecular mass of 2,800 | 12.0 |

From this composition having a pH of its solution equal to 3.5, plates are produced as described in Example 1 hereinbefore, each plate having a thickness of 0.5 mm, weight of 20 mg and the content of insulin is 30 units.

What is claimed is:

1. A pharmaceutical composition which provides a smooth hypoglycemic effect for treatment of diabetes comprising a self-adhesive shaped object for administration by adhesion to the mucous membrane of the mouth cavity, which is capable of resorption, which is of a sufficient size to provide an effective dose, and which comprises the following components in percent by weight:

crystalline insulin; 1 to 25.0
at least one additive for inhibiting deactivation of insulin by saliva selected from the group consisting of (a) 5-(para-[N-(3-methoxypyridazinyl-6)-sulphamido]-phenylazo)-salicyclic acid of the formula:

$$\text{HOOC-C}_6\text{H}_3(\text{OH})-\text{N}=\text{N}-\text{C}_6\text{H}_4-\text{SO}_2-\text{NH}-\text{C}_4\text{H}_2\text{N}_2-\text{OCH}_3$$

and

| | |
|---|---|
| (b) mixtures of (a) and calcium gluconate | 0.02 to 10.0 |
| a preservative for said insulin; | 0.1 to 15.0 |
| an additive for adjusting insulin solubility; and a coplymer of N—vinylpyrrolidone, acrylamide, and ethylacrylate, in the following proportions in percent by weight: | 0.01 to 10.0 |
| N—vinylpyrrolidone with acrylamide; | 70 to 99% |
| Ethylacrylate | 1 to 30% | the balance.

2. The pharmaceutical composition as claimed in claim 1, wherein the preservative is phenol in an amount of from 0.1 to 1%.

3. The pharmaceutical composition as claimed in claim 1, wherein the preservative is albumin in an amount of from 1 to 15%.

4. The pharmaceutical composition as claimed in claim 1, wherein the preservative a a mixture of phenol and albumin is used in an amount of from 0.1 to 15%.

5. The pharmaceutical composition as claimed in claim 1, wherein as the additive adjusting insulin solubility is selected from the group consisting of 0.5N hydrochloric acid and acetic acid in an amount ensuring a pH of the mixture within the range of from 2.0 to 4.0.

6. The pharmaceutical composition as claimed in claim 1, wherein the additive adjusting insulin solubility is glycine in an amount of from 1 to 10%.

7. The pharmaceutical composition as claimed in claim 1, further comprising glucose in an amount of from 2 to 20% by weight of the copolymer.

8. The pharmaceutical composition as claimed in claim 1, further comprising a polyester derived from polyethylene glycol and a dibasic acid with a molecular mass of from 2,000 to 5,000 in an amount of from 2 to 20% by weight of the copolymer.

9. The pharmaceutical composition as claimed in claim 1, further comprising polyvinylpyrrolidone in an amount of from 2 to 20% by weight of the copolymer.

10. The pharmaceutical composition as claimed in claim 1 shaped as a plate, said plate having a thickness of from 0.1 to 1.5 mm with a content of insulin ranging from 20 to 150 units.

11. A method of treating diabetes mellitus in a warm blooded animal comprising administering to said warm blooded animal, a therapeutically effective amount of the composition of claim 1 or 11.

12. The method of claim 11 further comprising contacting said composition with the mucous membrane of the oral cavity.

* * * * *